(12) United States Patent
Crabb et al.

(10) Patent No.: US 6,262,071 B1
(45) Date of Patent: Jul. 17, 2001

(54) METHODS OF USE OF ANTIMICROBIAL COMPOUNDS AGAINST PATHOGENIC AMYCOPLASMA BACTERIA

(75) Inventors: Donna M. Crabb; Lynn B. Duffy; Karen B. Searcy, all of Birmingham, AL (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/399,855

(22) Filed: Sep. 21, 1999

Related U.S. Application Data

(60) Provisional application No. 60/141,455, filed on Jun. 29, 1999.

(51) Int. Cl.[7] ............................. A61K 31/47; A61K 31/44
(52) U.S. Cl. ............................. 514/312; 514/300; 514/311
(58) Field of Search .................................. 514/312, 311, 514/300

(56) References Cited

U.S. PATENT DOCUMENTS

| 5,776,944 | * | 7/1998 | Hong et al. | 514/300 |
| 5,962,468 | * | 10/1999 | Hong et al. | 514/300 |

FOREIGN PATENT DOCUMENTS

| 0 688 772 A1 | 12/1995 | (EP) . |
| WO 98/42705 | 10/1998 | (WO) . |

\* cited by examiner

*Primary Examiner*—Kevin E. Weddington
(74) *Attorney, Agent, or Firm*—Edward R. Gimmi; Loretta J. Henderson; Charles M. Kinzig

(57) ABSTRACT

This invention relates, in part, to newly identified methods of using quinolone antibiotics, particularly a gemifloxacin compound against certain pathogenic bacteria.

13 Claims, No Drawings

METHODS OF USE OF ANTIMICROBIAL COMPOUNDS AGAINST PATHOGENIC AMYCOPLASMA BACTERIA

This application claims benefit of provisional application Ser. No. 60/141,455 filed Jun. 29, 1999.

This invention relates, in part, to newly identified methods of using quinolone antibiotics, particularly a gemifloxacin compound against Mycoplasma bacteria, such as *Mycolplasma pneumoniae*.

BACKGROUND OF THE INVENTION

Quinolones have been shown to be effective to varying degrees against a range of bacterial pathogens. However, as diseases caused by these pathogens are on the rise, there exists a need for antimicrobial compounds that are more potent than the present group of quinolones.

Gemifloxacin mesylate (SB-265805) is a novel fluoroquinolone useful as a potent antibacterial agent. Gemifloxacin compounds are described in detail in patent application PCT/KR98/00051 published as WO 98/42705. Patent application EP 688772 discloses novel quinoline(naphthyridine) carboxylic acid derivatives, including anhydrous (R,S)-7-(3-aminomethyl-4-methoxyiminopyrrolidin-1-yl)-1-cyclopropyl-6-fluoro-4-oxo-1,4-dihydro-1,8-naphthyridine-3-carboxylic acid of formula I.

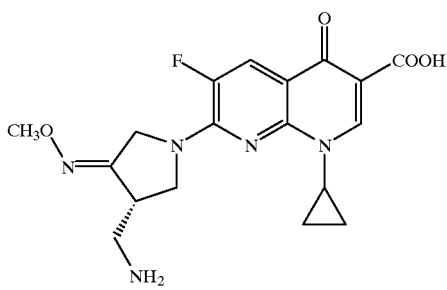

I

PCT/KR98/00051 discloses (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate and hydrates thereof including the sesquihydrate.

Provided herein is a significant discovery made using a gemifloxacin compound against Mycoplasma, demonstrating the activity of the gemifloxacin compound used was superior to a number of quinolones as described in more detail herein. Germifloxacin compounds are valuable compounds for the treatment of bacterial infection caused by a range of Mycoplasma pathogens, including those resistant to usual oral therapy, thereby filling an unmet medical need.

SUMMARY OF THE INVENTION

An object of the invention is a method for modulating metabolism of pathogenic Mycoplasma bacteria comprising the step of contacting pathogenic Mycoplasma bacteria with an antibacterially effective amount of a composition comprising a quinolone, particularly a gemifloxacin compound, or an antibacterially effective derivative thereof.

A further object of the invention is a method wherein said pathogenic Mycoplasma bacteria is selected from the group consisting of: *Mycoplasma pneumoniae, M. hominis, M. fermentans, M. genitaliun, M. penetrans* and *Ureaplasma urealyticum*.

Also provided by the invention is a method of treating or preventing a bacterial infection by pathogenic Mycoplasma bacteria comprising the step of administering an antibacterially effective amount of a composition comprising a quinolone, particularly a gemifloxacin compound to a mammal suspected of having or being at risk of having an infection with pathogenic Mycoplasma bacteria.

A preferred method is provided wherein said modulating metabolism is inhibiting growth of said bacteria or killing said bacteria.

A further preferred method is provided wherein said contacting said bacteria comprises the further step of introducing said composition into a mammal, particularly a human.

Further preferred methods are provided by the invention wherein said bacteria is selected from the group consisting of: *Mycoplasma pneumoniae, M. hominis, M. fermentans, M. genitalium, M. penetrans* and *Ureaplasma urealyticum*.

Various changes and modifications within the spirit and scope of the disclosed invention will become readily apparent to those skilled in the art from reading the following descriptions and from reading the other parts of the present disclosure.

DESCRIPTION OF THE INVENTION

The present invention provides, among other things, methods for using a composition comprising a quinolone, particularly a gemifloxacin compound against a range of pathogenic bacteria.

As used herein "gemifloxacin compound(s)" means a compound having antibacterial activity described in patent application PCT/KR98/00051 published as WO 98/42705, or patent application EP 688772.

This invention was based, in part, on analyses evaluating the in vitro activity of a gemifloxacin compound, as well as other new quinolones and macrolides using low-passaged clinical isolates and type strains of Mycoplasma species commonly found in the respiratory and urogenital tract of humans. Organisms used in the analyses included *Mycoplasma pneumoniae* (MPN), *M. homonis* (Mh), *M. fermentans* (Mf), *M. genitalium* (Mg), *M. penetrans* (Mp) and *Ureaplasma urealyticum* (Uu). Minimum Inhibitory Concentrations (MICs) were determined using a micro-broth dilution method. Assays for *Ureaplasma urealyticum* were performed in 10B media and all other mycoplasma assays were carried out in SP4 medium. Comparator drugs, to which gemifloxacin was compared, as well as also being useful in the methods of the invention, include levofloxacin (Lev), trovafloxacin (Tro), grepafloxacin (Gre), azithromycin (Azi), clarithromycin (Cla), tetracycline (Tet) and clindamycin (Cli). The results of these MIC assays are shown in Table 1.

TABLE 1

| Isolates (number) | MIC 90 (ug/ml) | | | | | | | |
|---|---|---|---|---|---|---|---|---|
| | Gem | Lev | Trov | Grep | Azith | Clar | Tet | Clin |
| MPN (103) | 0.125 | 0.5 | 0.25 | 0.125 | ≦0.008 | ≦0.008 | 0.25 | — |
| Mh (49) | ≦0.008 | 0.25 | 0.031 | 0.031 | — | — | 32 | ≦0.008 |
| Mf (19) | ≦0.008 | 0.031 | 0.016 | 0.016 | 2 | 64 | 0.063 | 0.031 |
| Uu (99) | 0.25 | 1 | 0.125 | 1 | 4 | 0.063 | 1 | — |
| MICs for Mg (2) | 0.063 | 1 | 0.063 | 0.125 | ≦0.008 | ≦0.008 | 0.125 | 0.25 |
| | 0.063 | 0.5 | 0.063 | 0.125 | ≦0.008 | ≦0.008 | 0.063 | 0.25 |
| MICs for Mp (1) | ≦0.008 | 0.031 | ≦0.008 | 0.016 | ≦0.008 | ≦0.008 | 0.125 | ≦0.008 |

Depending on the species tested, gemifloxacin had variable results when compared to the macrolides. Gemifloxacin was equally as active or more active in vitro when compared to tetracycline, clindamycin and the other quinolones.

The invention provides a method for modulating metabolism of pathogenic Mycoplasma bacteria. Skilled artisans can readily choose pathogenic Mycoplasma bacteria or patients infected with or suspected to be infected with these organisms to practice the methods of the invention. Alternatively, the bacteria useful in the methods of the invention may be those described herein.

The contacting step in any of the methods of the invention may be performed in many ways that will be readily apparent to the skilled artisan. However, it is preferred that the contacting step is a provision of a composition comprising a gemifloxacin compound to a human patient in need of such composition or directly to bacteria in culture medium or buffer.

For example, when contacting a human patient or contacting said bacteria in a human patient or in vitro, the compositions comprising a quinolone, particularly a gemifloxacin compound, preferably pharmaceutical compositions may be administered in any effective, convenient manner including, for instance, administration by topical, oral, anal, vaginal, intravenous, intraperitoneal, intramuscular, subcutaneous, intranasal or intradermal routes among others.

It is also preferred that these compositions be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a compound of the invention, a quinolone, preferably a gemifloxacin compound, and a pharmaceutically acceptable carrier or excipient. Such carriers may include, but are not limited to, saline, buffered saline, dextrose, water, glycerol, ethanol and combinations thereof. The formulation should suit the mode of administration.

Quinolone compounds, particularly gemifloxacin compounds and compostions of the methods of the invention may be employed alone or in conjunction with other compounds, such as bacterial efflux pump inhibtor compounds or antibiotic compounds, particularly non-quinolone compounds, e.g., beta-lactam antibiotic compounds.

In therapy or as a prophylactic, the active agent of a method of the invention is preferably administered to an individual as an injectable composition, for example as a sterile aqueous dispersion, preferably an isotonic one.

Alternatively, the gemifloxacin compounds or compositions in the methods of the invention may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the antibacterially effective amount is a daily dosage level of the active agent from 0.001 mg/kg to 10 mg/kg, typically around 0.1 mg/kg to 1 mg/kg, preferably about 1 mg/kg. A physician, in any event, will determine an actual dosage that is most suitable for an individual and will vary with the age, weight and response of the particular individual. The above dosages are exemplary of the average case. There can, of course, be individual instances where higher or lower dosage ranges are merited, and such are within the scope of this invention. It is preferred that the dosage is selected to modulate metabolism of the bacteria in such a way as to inhibit or stop growth of said bacteria or by killing said bacteria. The skilled artisan may identify this amount as provided herein as well as using other methods known in the art, e.g. by the application MIC tests.

A further embodiment of the invention provides for the contacting step of the methods to further comprise contacting an in-dwelling device in a patient. In-dwelling devices include, but are not limited to, surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters.

A quinolone, particularly a gemifloxacin compound or composition of the invention may be administered by injection to achieve a systemic effect against relevant bacteria, preferably a pathogenic Mycoplasma bacteria, shortly before insertion of an in-dwelling device. Treatment may be continued after surgery during the in-body time of the device. In addition, the composition could also be used to broaden perioperative cover for any surgical technique to prevent bacterial wound infections caused by or related to pathogenic Mycoplasma bacteria.

In addition to the therapy described above, a gemifloxacin compound or composition used in the methods of this invention may be used generally as a wound treatment agent to prevent adhesion of bacteria to matrix proteins, particularly pathogenic Mycoplasma bacteria, exposed in wound tissue and for prophylactic use in dental treatment as an alternative to, or in conjunction with, antibiotic prophylaxis.

Alternatively, a quinolone, particularly a gemifloxacin compound or composition of the invention may be used to bathe an indwelling device immediately before insertion. The active agent will preferably be present at a concentration of 1 µg/ml to 10 mg/ml for bathing of wounds or indwelling devices.

Also provided by the invention is a method of treating or preventing a bacterial infection by pathogenic Mycoplasma bacteria comprising the step of administering an antibacterially effective amount of a composition comprising a quinolone, particularly a gemifloxacin compound to a mammal, preferably a human, suspected of having or being at risk of having an infection with pathogenic Mycoplasma bacteria.

While a preferred object of the invention provides a method wherein said pathogenic Mycoplasma bacteria is selected from the group consisting of: *Mycoplasma pneumoniae, M. hominis, M. fermentans, M. genitalium, M. penetrans* and *Ureaplasma urealyticum*. Other pathogenic Mycoplasma bacteria may also be included in the methods. The skilled artisan may identify these organisms as provided herein as well as using other methods known in the art, e.g. MIC tests.

Preferred embodiments of the invention include, among other things, methods wherein said composition comprises gemifloxacin, or a pharmaceutically acceptable derivative thereof.

Each reference cited herein is hereby incorporated by reference in its entirety. Moreover, each patent application to which this application claims priority is hereby incorporated by reference in its entirety.

What is claimed is:

1. A method for modulating metabolism of pathogenic Mycoplasma bacteria comprising the step of contacting pathogenic Mycoplasma bacteria with an antibacterially effective amount of a composition comprising a gemifloxacin compound, or antibacterially effective derivatives thereof.

2. The method of claim 1 wherein said pathogenic Mycoplasma bacteria is a member of the genus Mycoplasma.

3. The method of claim 1 wherein said modulating metabolism is inhibiting growth of said bacteria.

4. The method of claim 1 wherein said modulating metabolism is killing said bacteria.

5. The method of claim 1 wherein said contacting said bacteria comprises the further step of introducing said composition into a mammal.

6. The method of claim 5 wherein said mammal is a human.

7. The method of claim 2 wherein said bacteria is selected from the group consisting of: *Mycoplasma hominis* and *Mycoplasma fermentans.*

8. The method of claim 1 wherein said bacteria is a member of the genus Ureaplasma.

9. The method of claim 8 wherein said bacteria is *Ureaplasma urealyticum.*

10. The method of claim 2 wherein said bacteria is selected from the group consisting of: *Mycoplasma pneuoniae, Mycoplasma genitalium,* and *Mycoplasma penetrans.*

11. The method according to claim 1, 2, 7, 8, 9 or 10 wherein the gemifloxacin compound is gemifloxacin or a pharmaceutically acceptable salt thereof.

12. The method according to claim 11 wherein the gemifloxacin compound is gemifloxacin mesylate or a hydrate thereof.

13. The method according to claim 12 wherein the gemifloxacin compound is gemifloxacin mesylate sesquihydrate.

* * * * *